US010993753B2

(12) United States Patent
Tempco et al.

(10) Patent No.: US 10,993,753 B2
(45) Date of Patent: May 4, 2021

(54) BONE SCREW AND METHOD OF MANUFACTURE

(71) Applicant: Warsaw Orthopedic, Inc., Warsaw, IN (US)

(72) Inventors: Dale A. Tempco, Germantown, TN (US); Rodney Ray Ballard, Lakeland, TN (US); Keith E. Miller, Germantown, TN (US); William Alan Rezach, Covington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 241 days.

(21) Appl. No.: 15/975,143

(22) Filed: May 9, 2018

(65) Prior Publication Data

US 2019/0343566 A1 Nov. 14, 2019

(51) Int. Cl.
*A61B 17/86* (2006.01)
*A61B 17/70* (2006.01)
*A61B 17/00* (2006.01)

(52) U.S. Cl.
CPC ...... *A61B 17/8625* (2013.01); *A61B 17/7059* (2013.01); *A61B 17/866* (2013.01); *A61B 17/7001* (2013.01); *A61B 2017/00526* (2013.01); *A61B 2017/00862* (2013.01)

(58) Field of Classification Search
CPC . A61B 17/8625; A61B 17/86; A61B 17/7001; A61B 17/7059; A61B 2017/00526; A61B 2017/00862
USPC ................................. 606/300–321
See application file for complete search history.

(56) References Cited

U.S. PATENT DOCUMENTS

| 7,850,717 B2 | 12/2010 | Dewey et al. |
| 2008/0177331 A1 | 7/2008 | Perez-Cruet et al. |
| 2010/0042167 A1 | 2/2010 | Nebosky et al. |
| 2010/0094420 A1 | 4/2010 | Grohowski, Jr. |
| 2011/0172798 A1 | 7/2011 | Staiger et al. |
| 2015/0018956 A1 | 1/2015 | Steinmann et al. |
| 2015/0032159 A1 | 1/2015 | Beger et al. |
| 2015/0150614 A1 | 6/2015 | Tsai et al. |
| 2015/0223907 A1 | 8/2015 | Kieser |

(Continued)

FOREIGN PATENT DOCUMENTS

| CN | 101500499 A | 8/2009 |
| CN | 104523342 A | 4/2015 |

(Continued)

OTHER PUBLICATIONS

Tempco, et al., Spinal Implant and Method of Manufacture, U.S. Appl. No. 15/666,281, filed Aug. 1, 2017, 39 pages.

(Continued)

*Primary Examiner* — Jessica Weiss
(74) *Attorney, Agent, or Firm* — Sorell, Lenna & Schmidt, LLP

(57) ABSTRACT

A bone screw comprises a shaft including a proximal portion, a distal portion and a wall including at least one thread having an external thread form having a lattice configuration. The thread form defining at least one void configured for bone growth therethrough. The distal portion is fabricated onto the proximal portion by an additive manufacturing method. In some embodiments, systems, spinal constructs, surgical instruments and methods are disclosed.

19 Claims, 5 Drawing Sheets

(56) References Cited

U.S. PATENT DOCUMENTS

| | | | |
|---|---|---|---|
| 2015/0313658 A1* | 11/2015 | Kolb | A61B 17/8625 606/309 |
| 2016/0099620 A1 | 4/2016 | Novello | |
| 2016/0157908 A1* | 6/2016 | Cawley | A61B 17/7032 606/301 |
| 2016/0367371 A1 | 12/2016 | de Beaubien et al. | |
| 2017/0165077 A1 | 6/2017 | McDonnell | |
| 2017/0245851 A1 | 8/2017 | Biedermann et al. | |
| 2018/0028242 A1 | 2/2018 | Parekh et al. | |
| 2018/0042702 A1 | 2/2018 | Stuebinger | |

FOREIGN PATENT DOCUMENTS

| | | |
|---|---|---|
| CN | 204337022 U | 5/2015 |
| CN | 204337069 U | 5/2015 |
| CN | 104758042 A | 7/2015 |
| CN | 104840243 A | 8/2015 |
| CN | 204581484 U | 8/2015 |
| CN | 204931871 U | 1/2016 |
| CN | 204931872 U | 1/2016 |
| CN | 105662621 A | 6/2016 |
| CN | 205698065 U | 11/2016 |
| CN | 106473787 A | 3/2017 |
| CN | 106580494 A | 4/2017 |
| CN | 106859792 A | 6/2017 |
| CN | 206576968 U | 10/2017 |
| CN | 206761724 U | 12/2017 |
| CN | 206761725 U | 12/2017 |
| CN | 206761797 U | 12/2017 |
| CN | 206761967 U | 12/2017 |
| EP | 2796104 B1 | 12/2016 |
| FR | 3036945 A1 | 12/2016 |
| KR | 20140141463 A | 12/2014 |
| WO | 2014076157 A1 | 5/2014 |
| WO | 2017161115 A1 | 9/2017 |
| WO | 2017161121 A1 | 9/2017 |
| WO | 2017192853 A1 | 11/2017 |

OTHER PUBLICATIONS

Tempco, et al., System and Method of Manufacture for Spinal Implant, U.S. Appl. No. 15/666,305, filed Aug. 1, 2017, 39 pages.
Tempco, et al., System and Method of Manufacture for Spinal Implant, U.S. Appl. No. 15/889,355, filed Feb. 6, 2018, 41 pages.
BoneZone Magazine, Commercialization Solutions for the Orthopaedic Industry www.BONEZONEpub.com, vol. 16 Issue 3 | Aug. 2017, 2 pages.
AmorChem, Porous_screw, McGill, Research Institute McGill University Health Centre—Press Release 2012, 2 pages.
International Search Report and Written Opinion of the International Searching Authority, European Patent Office, PCT/US2019/031230, dated Aug. 23, 2019.

* cited by examiner

BONE SCREW AND METHOD OF MANUFACTURE

TECHNICAL FIELD

The present disclosure generally relates to medical devices for the treatment of spinal disorders, and more particularly to a spinal implant system having spinal implants manufactured by a method including a plurality of manufacturing techniques.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including bone fasteners are often used to provide stability to a treated region. Such bone fasteners are traditionally manufactured using a medical machining technique. This disclosure describes an improvement over these prior technologies.

SUMMARY

In one embodiment, a bone screw is provided. The bone screw comprises a shaft including a proximal portion, a distal portion and a wall including at least one thread having an external thread form having a lattice configuration. The thread form defining at least one void configured for bone growth therethrough. The distal portion is fabricated onto the proximal portion by an additive manufacturing method. In some embodiments, systems, spinal constructs, spinal implants, surgical instruments and methods are disclosed.

In one embodiment, the bone screw comprises a shaft including at least one thread having an external thread form. The thread form having a lattice configuration. The shaft further including an outer surface defining a first opening and a second opening and defining at least one void therebetween. The at least one void being configured for bone growth therethrough.

In one embodiment, the bone screw comprises a shaft including a proximal portion, a distal portion and a wall including at least one thread having an external thread form including a crest and an inner portion. The thread form having a lattice configuration. The thread form defining at least one void disposed between the crest and the portion, the void being configured for bone growth therethrough, wherein the distal portion is formed onto the proximal portion by an additive manufacturing method.

BRIEF DESCRIPTION OF THE DRAWINGS

The present disclosure will become more readily apparent from the specific description accompanied by the following drawings, in which.

DETAILED DESCRIPTION

Figure 1:
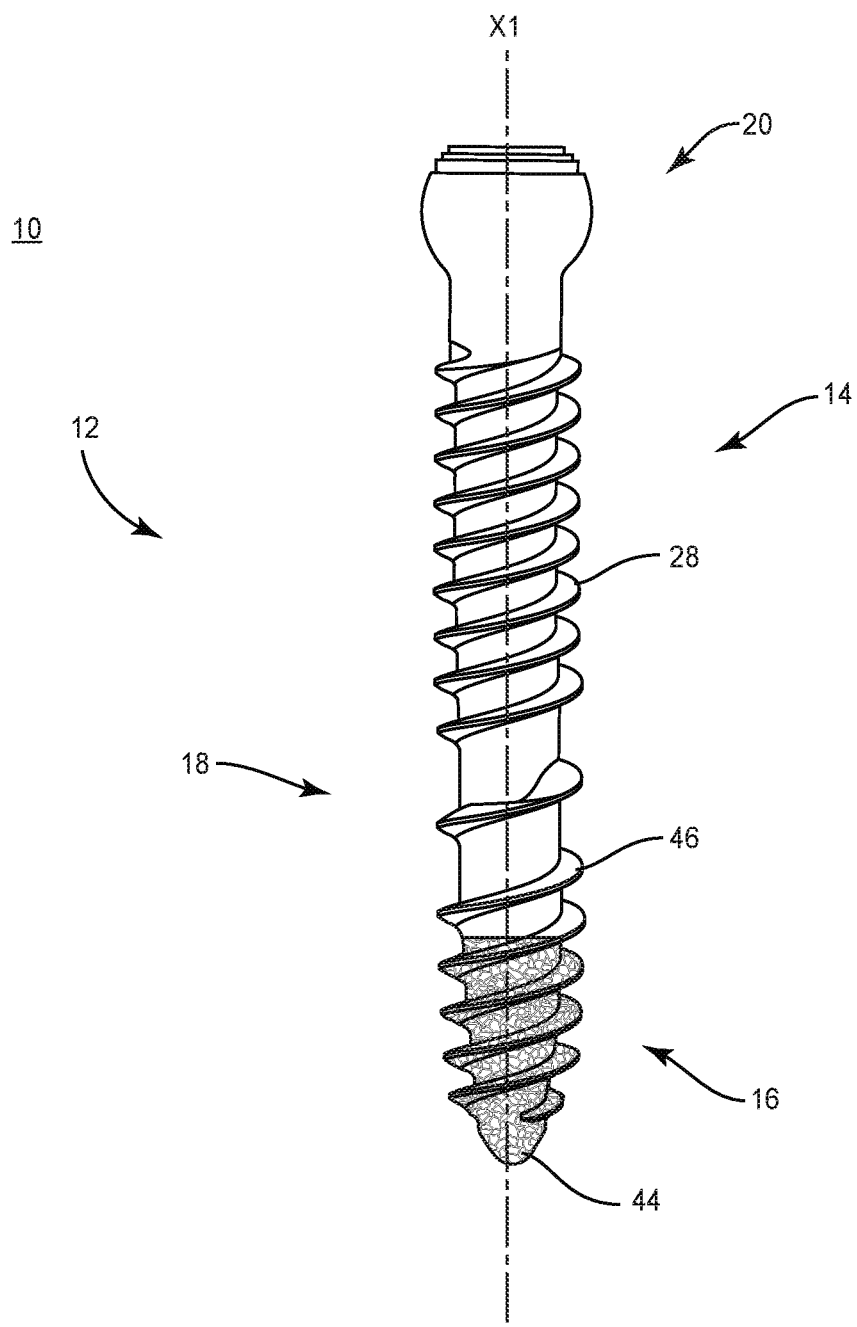
FIG. 1 is a side view of components of one embodiment of a system in accordance with the principles of the present disclosure.
Figure 2:
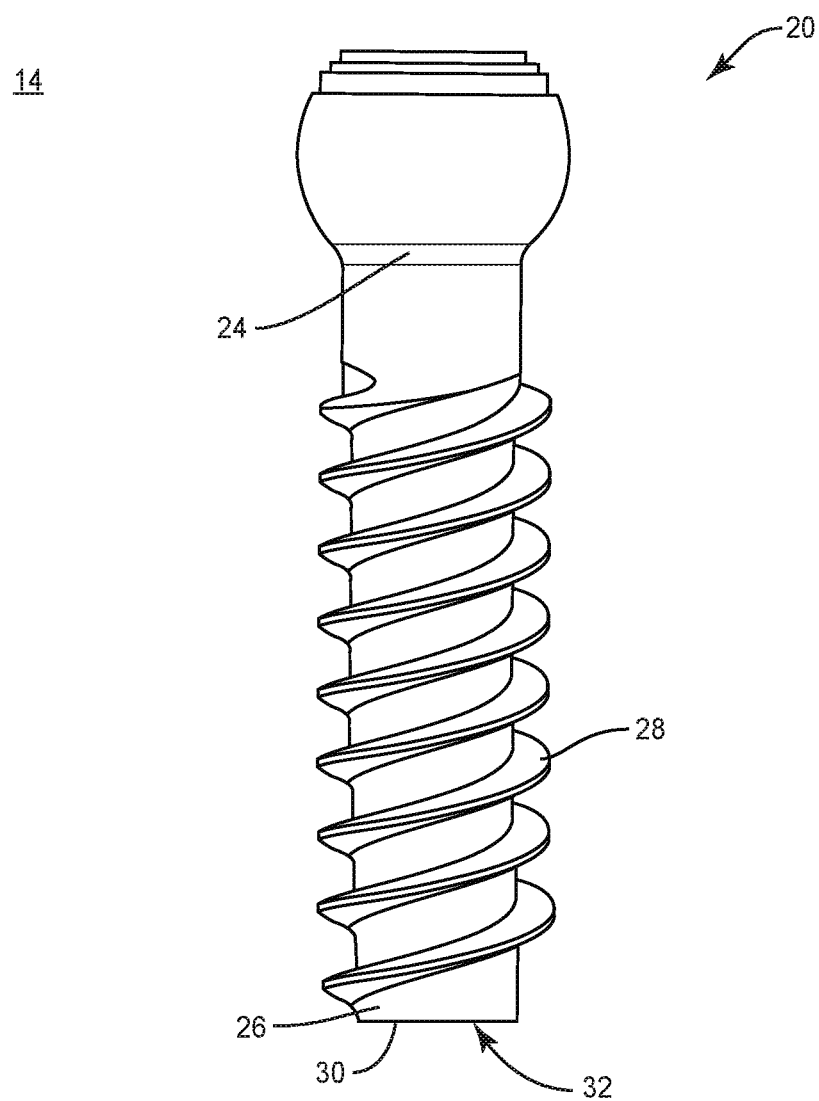
FIG. 2 is a side view of components of one embodiment of a system in accordance with the principles of the present disclosure.
Figure 3:
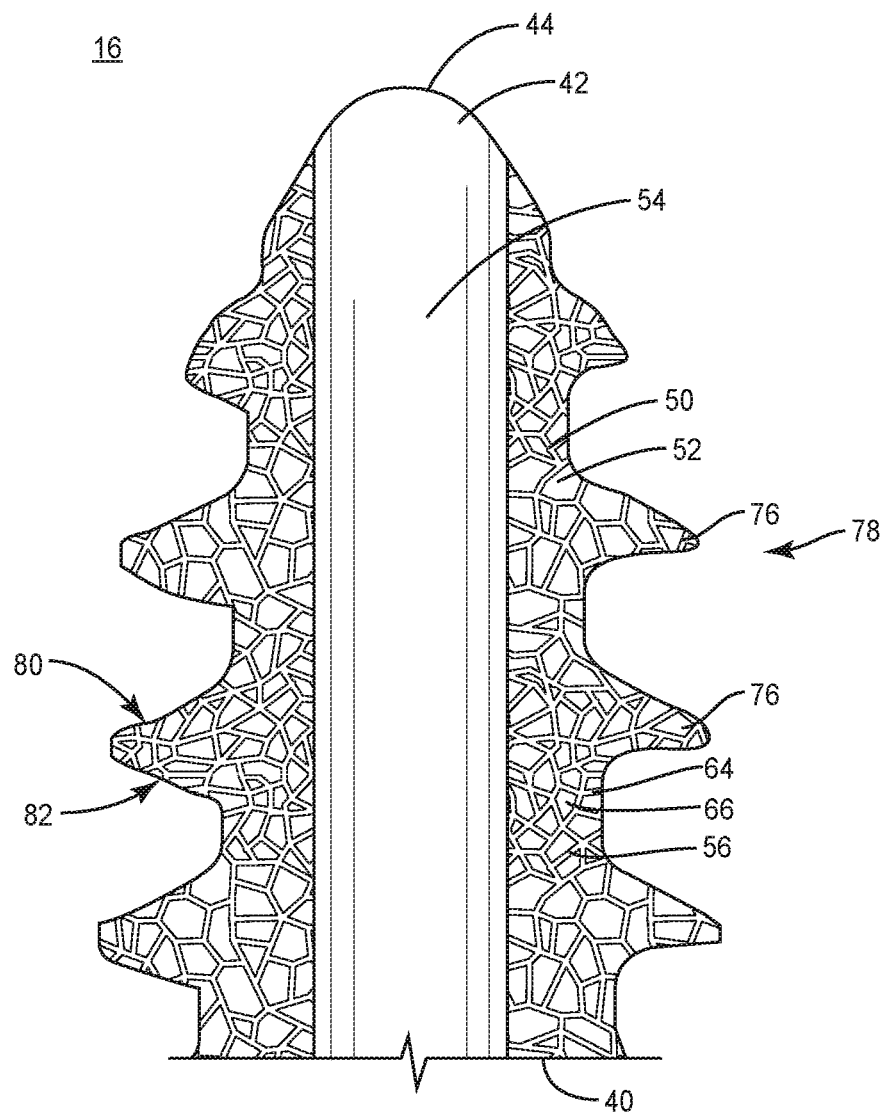
FIG. 3 is a break away cross section view of components of the system shown in FIG. 1.

The exemplary embodiments of a surgical system and related methods of use disclosed are discussed in terms of medical devices for the treatment of musculoskeletal disorders and more particularly, in terms of a spinal implant having a structure for bone through-growth. In some embodiments, the spinal implant system includes a spinal implant comprising a bone screw including a structure for bone through-growth.

In some embodiments, the spinal implant system of the present disclosure comprises a bone screw having a structure for bone through-growth that combines a manufacturing method, such as, for example, one or more traditional manufacturing features and materials and a manufacturing method, such as, for example, one or more additive manufacturing features and materials. In some embodiments, the bone screw is configured with features that facilitate bone to grow through the structure of the screw from opposing sides allowing the bone to connect through the screw. In some embodiments, the structure may be narrow, such as through the bone screw thread, which would allow for rapid through growth. In some embodiments, the structure may be deeper, such as though the minor diameter, which would provide a stronger bond. In some embodiments, the feature may be a void in the screw or it can be porous or structured such as to promote bone growth.

In some embodiments, the spinal implant system of the present disclosure is configured to enhance fixation of bone screws with bone. In some embodiments, the spinal implant system of the present disclosure includes a spinal implant configured for engagement with cortical bone and cancellous bone within the vertebra. In some embodiments, the spinal implant system of the present disclosure is configured to resist and/or prevent toggle on a bone screw when the bone screw is engaged with dense cortical bone and a less dense cancellous bone resulting from a load on the bone screw. In some embodiments, the spinal implant system of the present disclosure is configured to resist and/or prevent loosening of the bone screw from the cortical bone and in some instances, pull out from the vertebra. In some embodiments, the spinal implant system of the present disclosure is configured to facilitate bone through-growth to provide for an improved bone attachment to the bone screw. In some embodiments, the bone screw is anchored in the bone thereby reducing pull out.

In some embodiments, the spinal implant system of the present disclosure includes a bone screw having bone through-growth at a distal end of the screw to fix the distal end with tissue and to reduce toggle and potential failure of the screw. In some embodiments, the bone screw includes features that allow for bone to grow through the structure of the bone screw from opposing sides allowing bone to connect through those bone screw structures. In some embodiments, the bone screw includes features that may be narrow, such as through the bone screw thread, which would allow for rapid through growth. In some embodiments, the bone screw includes features that may be deeper, such as though the minor diameter, which would provide a larger volume of bone through-growth. In some embodiments, the bone screw includes features may be a void or cavity through opposite sides of the bone screw and/or a void or cavity that enters and exits from the same or adjoining surfaces. In some embodiments, the void or cavity may contain a scaffold for bone to attach or a porous structure on the surface of the void.

In some embodiments, the bone screw includes features or structures that may be disposed along a shaft portion of the bone screw. In some embodiments, the bone screw includes features or structures that may be disposed continuously along a surface of the bone screw, such as, for example, along a distal end. In some embodiments, the bone screw includes features or structures that may be disposed non-continuously along a portion of the bone screw. In some embodiments, the bone screw includes features or structures that may include bone scaffold.

In some embodiments, the spinal implant system comprises a spinal implant having a hybrid configuration that combines a manufacturing method, such as, for example, one or more traditional manufacturing features and materials and a manufacturing method, such as, for example, one or more additive manufacturing features and materials. In some embodiments, additive manufacturing includes 3-D printing. In some embodiments, additive manufacturing includes fused deposition modeling, selective laser sintering, direct metal laser sintering, selective laser melting, electron beam melting, layered object manufacturing and stereolithography. In some embodiments, additive manufacturing includes rapid prototyping, desktop manufacturing, direct manufacturing, direct digital manufacturing, digital fabrication, instant manufacturing and on-demand manufacturing. In some embodiments, the spinal implant system comprises a spinal implant being manufactured by a fully additive process and grown or otherwise printed.

In some embodiments, the spinal implant system of the present disclosure comprises a spinal implant, such as, for example, a bone screw manufactured by combining traditional manufacturing methods and additive manufacturing methods. In some embodiments, the bone screw is manufactured by applying additive manufacturing material in areas where the bone screw can benefit from materials and properties of additive manufacturing. In some embodiments, traditional materials are utilized where the benefits of these materials, such as physical properties and cost, are superior to those resulting from additive manufacturing features and materials.

In some embodiments, the spinal implants, surgical instruments and/or medical devices of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the spinal implants, surgical instruments and/or medical devices of the present disclosure may be employed with other osteal and bone related applications, including those associated with diagnostics and therapeutics. In some embodiments, the spinal implants, surgical instruments and/or medical devices of the present disclosure may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions such as maxillofacial and extremities. The spinal implants, surgical instruments and/or medical devices of the present disclosure may also be alternatively employed with procedures for treating the lumbar, cervical, thoracic, sacral and pelvic regions of a spinal column. The spinal implants, surgical instruments and/or medical devices of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a spinal implant, a method of manufacturing a spinal implant, related components and methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1-4, there are illustrated components of a spinal implant system 10 including spinal implants, surgical instruments and medical devices.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a spinal implant comprising a bone fastener, such as, for example, a bone screw 12. Bone screw 12 includes one or more cavities, for example, one or more pathways, openings, lattice and/or scaffold configured to facilitate bone growth through bone screw 12 to facilitate fixation of bone screw 12 with tissue, such as, for example, vertebral bone. In some embodiments, bone screw 12 allows bone growth from and/or through opposing sides such that bone is allowed to connect through bone screw 12. In some embodiments, bone screw 12 allows bone growth from and/or through bone screw threads for rapid through growth. In some embodiments, bone screw 12 allows bone growth from and/or through a minor diameter thereof to provide a larger volume of bone through-growth. In some embodiments, bone screw 12 allows bone growth that enters and exits from the same or adjoining surfaces. In some embodiments, bone screw 12 allows bone growth through a scaffold for bone to attach or a porous structure.

Bone screw 12 defines a longitudinal axis X1. Bone screw 12 includes a screw shaft 18 having a proximal portion 14 and a distal portion 16. In some embodiments, bone screw 12 is manufactured by a manufacturing process to enhance fixation and/or facilitate bone growth, as described herein. In some embodiments, bone screw 12 is manufactured by an additive manufacturing method. In some embodiments, proximal portion 14 is fabricated by a first manufacturing method and distal portion 16 fabricated by a second manufacturing method to enhance fixation and/or facilitate bone growth, as described herein.

In some embodiments, the manufacturing method can include a traditional machining method, such as, for example, subtractive, deformative or transformative manufacturing methods. In some embodiments, the traditional manufacturing method may include cutting, grinding, rolling, forming, molding, casting, forging, extruding, whirling, grinding and/or cold working. In some embodiments, the traditional manufacturing method includes portion 14 being formed by a medical machining process. In some embodiments, medical machining processes can include use of computer numerical control (CNC) high speed milling machines, Swiss machining devices, CNC turning with living tooling and/or wire EDM 4th axis. In some embodiments, the manufacturing method for fabricating portion 14 includes a finishing process, such as, for example, laser marking, tumble blasting, bead blasting, micro blasting and/or powder blasting.

For example, portion 14 is formed by a manufacturing method, which includes feeding a wire, rod, bar, or wire or rod bar stock into a machine that cuts the wire at a designated length to form a screw blank and then forms a head of the screw blank into a selected configuration. Portion 14 is manufactured to include a head 20 and a portion of screw shaft 18. Portion 14 extends between an end 24 and an end 26. End 24 includes head 20.

Portion 14 includes threads 28, which are fabricated by traditional machining methods, as described herein. Threads 28 extend along all or a portion of portion 14. Threads 28 are oriented with portion 14 and disposed for engagement with tissue. In some embodiments, threads 28 include a fine, closely-spaced configuration and/or shallow configuration to facilitate and/or enhance engagement with tissue. In some embodiments, threads 28 include a smaller pitch or more thread turns per axial distance to provide a stronger fixation with tissue and/or resist loosening from tissue. In some embodiments, threads 28 include an increased pitch and an equal lead between thread turns. In some embodiments, threads 28 are continuous along portion 14. In some embodiments, threads 28 are continuous along shaft 18 via a second manufacturing method, as described herein. In some embodiments, threads 28 may be intermittent, staggered, discontinuous and/or may include a single thread turn or a plurality of discrete threads. In some embodiments, other penetrating elements may be located on and/or manufactured with portion 14, such as, for example, a nail configuration, barbs, expanding elements, raised elements, ribs, and/or spikes to facilitate engagement of portion 14 with tissue.

End 26 includes a surface 30 that defines a distal end 32. In some embodiments, surface 30 may be disposed along a length of portion 14 or at a distalmost surface of portion 14. In some embodiments, distal end 32 extends perpendicular to axis X1. In some embodiments, distal end 32 may be disposed in various orientations relative to axis X1, such as, for example, transverse and/or at angular orientations, such as acute or obtuse. In one embodiment, distal end 32 is disposed at an acute angular orientation relative to axis X1.

Distal end 32 is configured for providing a fabrication platform for forming portion 16 thereon with an additive manufacturing method, as described herein. Distal end 32 has a substantially planar configuration for material deposition and/or heating during an additive manufacturing process for fabricating portion 16 onto distal end 32. In some embodiments, all or only a portion of distal end 32 may have alternate surface configurations, such as, for example, angled, irregular, uniform, non-uniform, offset, staggered, tapered, arcuate, undulating, mesh, porous, semi-porous, dimpled, pointed and/or textured. In some embodiments, distal end 32 may include a nail configuration, barbs, expanding elements, raised elements, ribs, and/or spikes to provide a fabrication platform for forming portion 16 thereon with an additive manufacturing method, as described herein. In some embodiments, all or only a portion of distal end 32 may have alternate cross section configurations, such as, for example, oval, oblong triangular, square, polygonal, irregular, uniform, non-uniform, offset, staggered, and/or tapered.

Portion 16 is fabricated with a second manufacturing method by disposing a material onto distal end 32, as described herein. Portion 16 is configured for fabrication on distal end 32 such that portion 16 is fused with surface 30. Portion 16 is formed on distal end 32 by an additive manufacturing method. Portion 16 is formed on distal end 32 to extend between an end 40 and end 42 according to instructions received from the computer and processor, and end 40 is fused with surface 30. End 42 includes a distal tip 44.

Portion 16 includes a wall 50 having a surface 52. In some embodiments, wall 50 extends circumferentially to define portion 16. In some embodiments, wall 50 is disposed about a solid inner core 54. In some embodiments, wall 50 defines a thickness, which may be uniform, undulating, tapered, increasing, decreasing, variable, offset, stepped, arcuate, angled and/or staggered. In some embodiments, surface 52 may be rough, textured, porous, semi-porous, dimpled, knurled, toothed, grooved and/or polished.

Portion 16 is fabricated according to instructions received from the computer and processor based on the digital rendering and/or data of the selected configuration, via the additive manufacturing process described herein to include a thread 76 that extends between end 40 and distal tip 44.

Surface 52 includes a non-solid configuration, such as, for example, a lattice 56. In some embodiments, the non-solid configuration may include a porous structure and/or a trabecular configuration. Disclosures herein involving a lattice, or other particular type of non-solid structure, are meant to disclose at the same time analogous embodiments in which other non-solid structure in addition or instead of the particular type of structure.

In various embodiments, the non-solid configuration is configured to provide one or a plurality of pathways to facilitate bone through growth within, and in some embodiments all of the way through, from one surface to an opposite surface of bone screw 12. Lattice 56 is continuous along surface 52 of portion 16 between end 40 and distal tip 44. In some embodiments, lattice 56 extends along all or a portion of inner core 54. Thread 46 is connected with lattice 56 to facilitate fixation of threads 46 with tissue. In some embodiments, lattice 56 may include one or more portions, layers and/or substrates. In some embodiments, one or more portions, layers and/or substrates of lattice 56 may be disposed side by side, offset, staggered, stepped, tapered, end to end, spaced apart, in series and/or in parallel. In some embodiments, lattice 56 defines a thickness, which may be uniform, undulating, tapered, increasing, decreasing, variable, offset, stepped, arcuate, angled and/or staggered. In some embodiments, one or more layers of lattice 56 are disposed in a side by side, parallel orientation within wall 50. Lattice 56 includes one or more layers of a matrix of material.

In some embodiments, lattice 56 includes a plurality of nodes 64 and openings 66, which can be disposed in rows and columns, and/or in a random configuration. In some embodiments, nodes 64 and openings 66 are disposed in a series orientation. In some embodiments, nodes 64 and openings 66 are disposed in a parallel orientation.

In some embodiments, lattice 56 may form a rasp-like configuration. In some embodiments, lattice 56 is configured to engage tissue, such as, for example, cortical bone and/or cancellous bone, such as, to cut, shave, shear, incise and/or disrupt such tissue. In some embodiments, all or a portion of each lattice 56 may have various configurations, such as, for example, cylindrical, round, oval, oblong, triangular, polygonal having planar or arcuate side portions, irregular, uniform, non-uniform, consistent, variable, horseshoe shape, U-shape or kidney bean shape. In some embodiments, lattice 56 may be rough, textured, porous, semi-porous, dimpled, knurled, toothed, grooved and/or polished to facilitate engagement and cutting of tissue. In some embodiments, lattice 56 forms a tunnel configured to guide, drive and/or direct the cut tissue into openings 66 to facilitate fusion of bone screw 12 with tissue, such as, for example, vertebrae.

Figure 4:
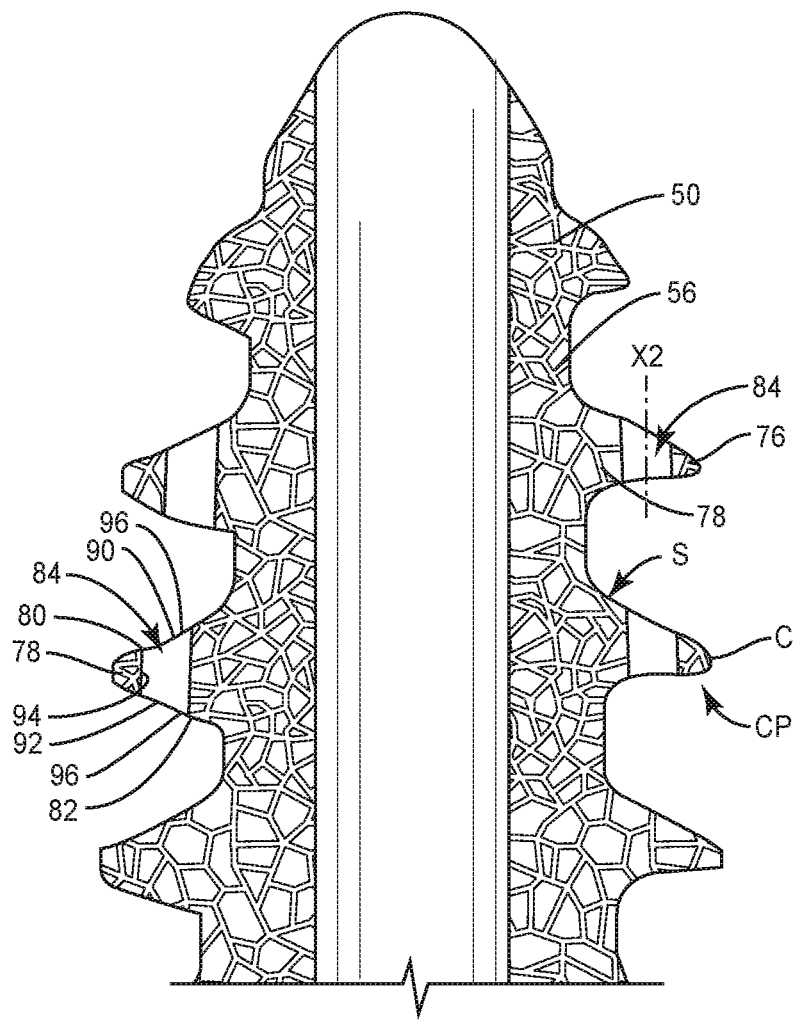
FIG. 4 is a break away cross section view of components of the system shown in FIG. 1.

Thread 76 includes an external thread form 78. Thread form 78 includes a leading edge having a surface 80 and a trailing edge having a surface 82. Surface 80 defines an opening 90. Surface 82 defines an opening 92. In some embodiments, openings 90, 92 are axially aligned. In some embodiments, openings 90, 92 are disposed circumferentially about thread form 78. Thread form 78 includes a surface 94 that defines a pathway and/or a void 84. In some embodiments, void 84 defines an axis X2. In some embodiments, axis X2 is disposed parallel relative to axis X1. In some embodiments, axis X2 is disposed axially along axis X1. In some embodiments, void 84 extends between openings 90, 92, as shown in FIG. 4. In some embodiments, axis X2 may be disposed in various orientations relative to axis X1 and/or surfaces 80, 82, such as, for example, transverse and/or at angular orientations, such as acute or obtuse. In some embodiments, void 84 extends completely through thread form 78. In some embodiments, at least one void 84 extends partially through thread form 78. In some embodiments, thread form 78 includes a plurality of spaced apart pathways and/or voids 84. In some embodiments, voids 84 may be positioned in any of a variety of ways, such as, for example, evenly spaced around at least a portion of thread form 78 and/or on leading and/or trailing surfaces 80, 82.

Thread form 78 includes a crest portion CP and an inner thread portion S. Crest portion CP includes a crest C. In some embodiments, crest C includes a lattice configuration and inner thread portion S includes a lattice configuration. In some embodiments, crest portion CP includes a solid configuration relative to inner thread portion S. In some embodiments, inner thread portion S includes a solid configuration relative to crest portion CP. In some embodiments, void 84 is disposed axially relative to crest portion CP and/or inner thread portion S. In some embodiments, void 84 may be disposed in various orientations relative to crest portion CP and/or inner thread portion S, such as, for example, transverse and/or at angular orientations, such as acute or obtuse. Void 84 in various embodiments is disposed between a section of the crest portion CP and an adjacent section of the inner thread portion S. Void 84 in various embodiments is disposed at and/or adjacent an intersection or interface between inner thread portion S and crest portion CP.

Void 84 is configured for disposal of tissue to promote bone growth to enhance fusion of bone screw 12, as described herein. In some embodiments, external grating materials or biologics may be prepacked with bone screw 12. In some embodiments, surface 80 and/or surface 82 includes at least one tissue gathering member. In some embodiments, the tissue gathering member may include a cutting edge 96. In some embodiments, cutting edge 96 may include a rasp-like configuration. In some embodiments, cutting edge 96 is configured to engage tissue, such as, for example, cortical bone and/or cancellous bone, such as, to cut, shave, shear, incise and/or disrupt such tissue. In some embodiments, all or a portion of cutting edge 96 may have various configurations, such as, for example, cylindrical, round, oval, oblong, triangular, polygonal having planar or arcuate side portions, irregular, uniform, non-uniform, consistent, variable, horseshoe shape, U-shape or kidney bean shape. In some embodiments, cutting edge 96 may be rough, textured, porous, semi-porous, dimpled, knurled, toothed, grooved and/or polished to facilitate engagement and cutting of tissue. In some embodiments, cutting edge 96 forms a tunnel configured to guide, drive and/or direct the cut tissue into void 84 to facilitate fusion of bone screw 12 with tissue, such as, for example, vertebrae.

For example, manipulation of bone screw 12, including rotation and/or translation causes cutting edge 96 to cut tissue and/or shave bone such that the cut tissue is guided and/or directed into void 84 to promote bone growth and enhance fusion of bone screw 12. In some embodiments, the tissue is imbedded into void 84 to promote bone growth and enhance fusion of bone screw 12. In some embodiments, lattice 56 disposed within void 84 forms a scaffold to facilitate bone growth therein.

In some embodiments, thread 76 is fabricated to include a fine, closely-spaced and/or shallow configuration to facilitate and/or enhance engagement with tissue. In some embodiments, thread 76 is fabricated to include an increased pitch and an equal lead between thread turns than thread 28, as shown in FIG. 1. In some embodiments, thread 76 is fabricated to include a smaller pitch or more thread turns per axial distance than thread 28 to provide a stronger fixation with tissue and/or resist loosening from tissue. In some embodiments, thread 76 is fabricated to be continuous along portion 16. In some embodiments, thread 76 is fabricated to be continuous along portion 16. In some embodiments, thread 76 is fabricated to be intermittent, staggered, discontinuous and/or may include a single thread turn or a plurality of discrete threads. In some embodiments, portion 16 is fabricated to include penetrating elements, such as, for example, a nail configuration, barbs, expanding elements, raised elements, ribs, and/or spikes. In some embodiments, thread 46 is fabricated to be self-tapping or intermittent at distal tip 44. In some embodiments, distal tip 44 may be rounded. In some embodiments, distal tip 44 may be self-drilling. In some embodiments, distal tip 44 includes a solid outer surface.

In some embodiments, additive manufacturing includes 3-D printing, as described herein. In some embodiments, additive manufacturing includes fused deposition modeling, selective laser sintering, direct metal laser sintering, selective laser melting, electron beam melting, layered object manufacturing and stereolithography. In some embodiments, additive manufacturing includes rapid prototyping, desktop manufacturing, direct manufacturing, direct digital manufacturing, digital fabrication, instant manufacturing or on-demand manufacturing. In some embodiments, portion 16 is manufactured by additive manufacturing, as described herein, and mechanically attached with surface 30 by, for example, welding, threading, adhesives and/or staking.

In one embodiment, one or more manufacturing methods for fabricating distal portion 16, proximal portion 14 and/or other components of bone screw 12 include imaging patient anatomy with imaging techniques, such as, for example, x-ray, fluoroscopy, computed tomography (CT), magnetic resonance imaging (MRI), surgical navigation, bone density (DEXA) and/or acquirable 2-D or 3-D images of patient anatomy. Selected configuration parameters of distal portion 16, proximal portion 14 and/or other components of bone screw 12 are collected, calculated and/or determined. Such configuration parameters can include one or more of patient anatomy imaging, surgical treatment, historical patient data, statistical data, treatment algorithms, implant material, implant dimensions, porosity and/or manufacturing method. In some embodiments, the configuration parameters can include implant material and porosity of distal portion 16 determined based on patient anatomy and the surgical treatment. In some embodiments, the implant material includes a selected porosity of distal portion 16, as described herein. In some embodiments, the selected configuration parameters of distal portion 16, proximal portion 14 and/or other components of bone screw 12 are patient specific. In some embodiments, the selected configuration parameters of distal portion 16, proximal portion 14 and/or other components of bone screw 12 are based on generic or standard configurations and/or sizes and not patient specific. In some embodiments, the selected configuration parameters of distal portion 16, proximal portion 14 and/or other components of bone screw 12 are based on one or more configurations and/or sizes of components of a kit of spinal implant system 10 and not patient specific.

For example, based on one or more selected configuration parameters, as described herein, a digital rendering and/or data of a selected distal portion 16, proximal portion 14 and/or other components of bone screw 12, which can include a 2-D or a 3-D digital model and/or image, is collected, calculated and/or determined, and generated for display from a graphical user interface, as described herein, and/or storage on a database attached to a computer and a processor (not shown), as described herein. In some embodiments, the computer provides the ability to display, via a monitor, as well as save, digitally manipulate, or print a hard copy of the digital rendering and/or data. In some embodiments, a selected distal portion 16, proximal portion 14 and/or other components of bone screw 12 can be designed virtually in the computer with a CAD/CAM program, which is on a computer display. In some embodiments, the processor may execute codes stored in a computer-readable memory medium to execute one or more instructions of the computer, for example, to transmit instructions to an additive manufacturing device, such as, for example, a 3-D printer. In some embodiments, the database and/or computer-readable medium may include RAM, ROM, EPROM, magnetic, optical, digital, electromagnetic, flash drive and/or semiconductor technology. In some embodiments, the processor can instruct motors (not shown) that control movement and rotation of spinal implant system 10 components, for example, a build plate, distal end 32 and/or laser emitting devices, as described herein.

Portion 14 is fabricated with threads 28 by a first manufacturing method, as described herein. Portion 14 is connected with a part, such as, for example, a build plate in connection with an additive forming process and a second manufacturing method for fabricating distal portion 16. Portion 16 is built up layer by layer and the melting process is repeated slice by slice, layer by layer, until the final layer of a material is melted and portion 16 is complete. Portion 16 is formed on distal end 32 to extend between an end 40 and end 42 according to instructions received from the computer and processor, and end 40 is fused with surface 30. In some embodiments, the material is subjected to direct metal laser sintering (DMLS®), selective laser sintering (SLS), fused deposition modeling (FDM), or fused filament fabrication (FFF), or stereolithography (SLA).

In some embodiments, portion 16 is fabricated in a configuration having a porosity via the additive manufacturing method, as described herein. In some embodiments, portion 16 is fabricated having a porosity with a porogen that is spheroidal, cuboidal, rectangular, elongated, tubular, fibrous, disc-shaped, platelet-shaped, polygonal or a mixture thereof. In some embodiments, a porosity of portion 16 is based on a plurality of macropores, micropores, nanopores structures and/or a combination thereof.

In some embodiments, bone screw 12 includes an implant receiver (not shown) connectable with head 20. In some embodiments, bone screw 12 can include various configurations, such as, for example, a posted screw, a pedicle screw, a bolt, a bone screw for a lateral plate, an interbody screw, a uni-axial screw, a fixed angle screw, a multi-axial screw, a side loading screw, a sagittal adjusting screw, a transverse sagittal adjusting screw, an awl tip, a dual rod multi-axial screw, midline lumbar fusion screw and/or a sacral bone screw. In some embodiments, the implant receiver can be attached by manual engagement and/or non-instrumented assembly, which may include a practitioner, surgeon and/or medical staff grasping the implant receiver and shaft 18 and forcibly snap or pop fitting the components together. In some embodiments, spinal implant system 10 comprises a kit including a plurality of bone screws 12 of varying configuration, as described herein. In some embodiments, bone screw 12 is selected from the kit and employed with a treatment at the surgical site.

In one embodiment, bone screw 12 is fabricated to define a passageway through all or a portion of shaft 18 such that bone screw 12 includes a cannulated configuration and a plurality of lateral fenestrations in communication with the passageway.

In assembly, operation and use, spinal implant system 10 is employed to treat an affected section of vertebrae. A medical practitioner obtains access to a surgical site including the vertebrae in any appropriate manner, such as through incision and retraction of tissues. The components of surgical system 10 including bone screw 12 are employed to augment a surgical treatment. Bone screw 12 can be delivered to a surgical site as a pre-assembled device or can be assembled in situ. Spinal implant system 10 may be may be completely or partially revised, removed or replaced.

Surgical system 10 may be used with surgical methods or techniques including open surgery, mini-open surgery, minimally invasive surgery and percutaneous surgical implantation, whereby the vertebrae is accessed through a mini-incision, or sleeve that provides a protected passageway to the area. Once access to the surgical site is obtained, a surgical treatment, for example, corpectomy and/or discectomy, can be performed for treating a spine disorder.

Bone screw 12 is connected with a surgical instrument, such as, for example, a driver (not shown) and is delivered to the surgical site. Bone screw 12 is manipulated including rotation and/or translation for engagement with cortical bone and/or cancellous bone. Manipulation causes cutting edge 96 to cut tissue and/or shave bone such that the cut tissue is guided and/or directed into void 84. The tissue becomes imbedded into void 84 to promote bone growth and enhance fusion of bone screw 12 to resist and/or prevent toggle. Manipulation causes lattice 56 to guide, drive and/or direct the cut tissue into openings 66 to facilitate fusion and promote bone growth and enhance fusion of bone screw 12 to resist and/or prevent toggle.

Figure 5:
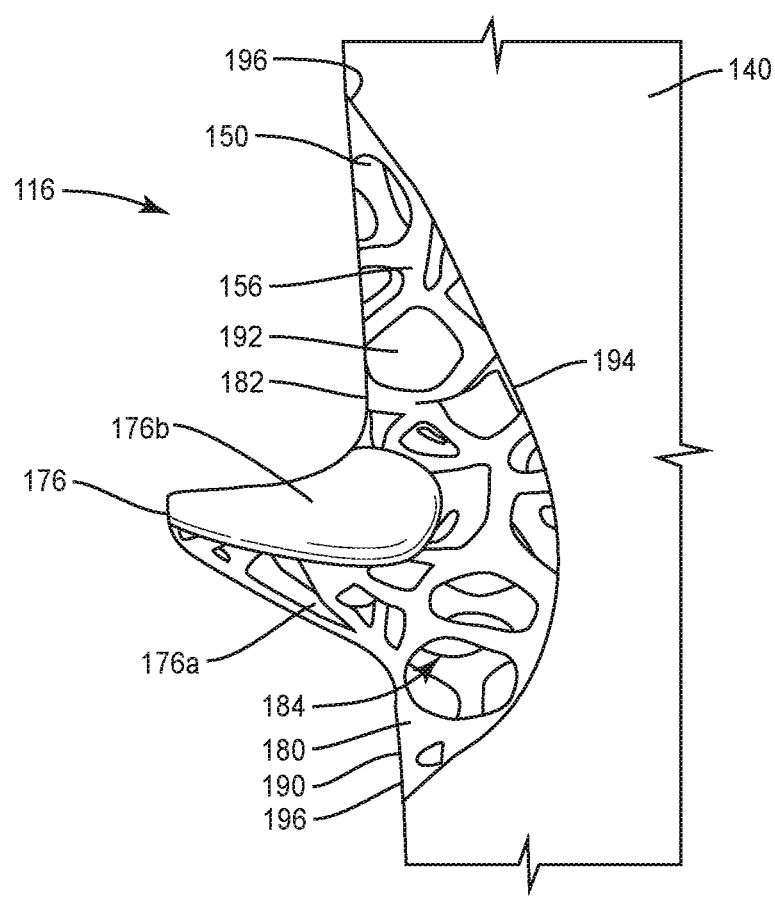
FIG. 5 is a break away side view of components of one embodiment of a system in accordance with the principles of the present disclosure.

In one embodiment, as shown in FIG. 5, spinal implant system 10, similar to the systems and methods described herein, includes a bone screw 112, similar to bone screw 12 described herein. Bone screw 112 includes portion 14, as described herein, and a portion 116. Portion 116 extends between an end 140 and an end (not shown). End 142 includes a distal tip (not shown).

Portion 116 includes a wall 150, similar to wall 50 described herein, having a non-solid configuration, as described herein, such as, for example, a lattice 156, similar to lattice 56 described herein. Portion 116 includes a thread 176 having an external thread form 178. Thread form 178 includes a leading edge 178*a* and a trailing edge 178*b*. A surface 180 is disposed adjacent to leading edge 178*a*. A surface 182 is disposed adjacent to trailing edge 178*b*. Surface 180 defines an opening 190. Surface 182 defines an opening 192. Wall 150 includes a surface 194 that defines a pathway 184, similar to void 84 described herein. Pathway 184 extends between openings 190, 192 and is disposed about thread form 178 in an arcuate configuration. In some embodiments, pathway 184 may be disposed in various orientations relative to axis X1 and/or surfaces 180, 182, such as, for example, axial, transverse and/or at angular orientations, such as acute or obtuse.

Pathway 184 is configured for disposal of tissue to promote bone growth to enhance fusion of bone screw 112, as described herein. In some embodiments, surface 180 and/or surface 182 includes at least one tissue gathering member, such as, for example, a cutting edge 196, similar to cutting edge 96 described herein, to guide, drive and/or direct the cut tissue into pathway 184 to facilitate fusion of bone screw 112 with tissue.

In some embodiments, portion 116 is formed on distal end 32 by an additive manufacturing method, as described herein. In some embodiments, portion 116 is fabricated according to instructions received from the computer and processor based on the digital rendering and/or data of the selected configuration, via the additive manufacturing process, as described herein. Portion 116 is configured for fabrication on distal end 32 such that portion 116 is fused with surface 30, as described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone screw comprising:
a shaft including a proximal portion, a distal portion and a wall including at least one thread having an external thread form comprising a plurality of threads, the threads each including a root and a crest opposite the root, the roots each extending from an outer surface of the wall,
at least a portion of the wall having a lattice configuration
at least a portion of the thread form having a lattice configuration,
wherein the lattice configuration of the portion of the wall and the lattice configuration of the portion of the thread form together define a lattice extending along a portion of the shaft,
wherein the portion of the shaft comprising the lattice is entirely non-solid,
the thread form defining at least one void formed therethrough along the portion of the shaft comprising the lattice, the at least one void configured for bone growth therethrough, and
wherein the distal portion is fabricated onto the proximal portion by an additive manufacturing method.

2. A bone screw as recited in claim 1, wherein the thread form includes a first surface and a second surface, and wherein the at least one void extends between the first and second surfaces.

3. A bone screw as recited in claim 1, wherein the at least one void extends completely through the thread form.

4. A bone screw as recited in claim 1, wherein the at least one void includes an axial pathway extending through the thread form.

5. A bone screw as recited in claim 1, wherein the at least one void includes a plurality of spaced apart pathways extending through the thread form.

6. A bone screw as recited in claim 1, wherein the shaft further includes a solid inner core, the wall being disposed about the solid inner core.

7. A bone screw as recited in claim 1, wherein the lattice extends continuously along a distal portion of the shaft.

8. A bone screw as recited in claim 1, wherein the distal portion includes a distal tip.

9. A bone screw as recited in claim 8, wherein the distal tip includes a solid outer surface.

10. A bone screw as recited in claim 1, wherein the distal portion is manufactured by a method including applying a material in a layer by layer formation.

11. A bone screw as recited in claim 1, wherein the lattice extends continuously from the root of one of the threads to the root of another one of the threads.

12. A bone screw as recited in claim 1, wherein the at least one void is positioned on each of the threads between the respective roots and crests of the threads.

13. A bone screw comprising:
a shaft including a proximal portion, a distal portion, and an external thread form comprising a plurality of threads,
the threads each including a root and a crest opposite the root, the roots each extending from an outer surface of the shaft,
at least a portion of the shaft having a lattice configuration,
at least a portion of the thread form having a lattice configuration,
wherein the lattice configuration of the portion of the shaft and the lattice configuration of the portion of the thread form together define a lattice extending along a portion of the shaft,
wherein the portion of the shaft comprising the lattice is entirely non-solid,
the shaft further including an outer surface defining a first opening and a second opening, and
the shaft defining at least one void extending between the first opening and the second opening, the at least one void being configured for bone growth therethrough,
wherein the distal portion is formed onto the proximal portion by an additive manufacturing method.

14. A bone screw as recited in claim 13, wherein the at least one void extends through the outer surface about the thread form.

15. A bone screw as recited in claim 13, wherein at least one of the plurality of threads comprises the at least one void.

16. A bone screw as recited in claim 13, wherein the lattice configuration of the portion of the shaft extends to the first opening and to the second opening.

17. A bone screw as recited in claim 13, wherein the distal portion comprises the at least one void and a distal tip.

18. A bone screw as recited in claim 17, wherein the distal portion is fabricated from an additive manufacturing method including adding a material in a layer by layer formation.

19. A bone screw comprising:
a shaft including a proximal portion, a distal portion and a wall including an external thread form comprising a plurality of threads,
the threads each including a root and a crest opposite the root, the roots each extending from an outer surface of the wall,
at least a portion of the wall having a lattice configuration,
at least a portion of the threads each having a lattice configuration,
wherein the lattice configuration of the portion of the wall and the lattice configuration of the portion of the thread form together define a lattice extending along a portion of the shaft,
wherein the portion of the shaft comprising the lattice is entirely non-solid,
the thread form defining at least one void disposed on each of the threads between the respective crests and roots of the threads,
the at least one void being configured for bone growth therethrough, and
wherein the distal portion is formed onto the proximal portion by an additive manufacturing method.

* * * * *